(12) United States Patent
McCaffrey (10) Patent No.: US 9,259,180 B2
(45) Date of Patent: Feb. 16, 2016

(54) DEVICE AND METHOD FOR DISPLAYING BIOFEEDBACK

(71) Applicant: Brenda McCaffrey, Phoenix, AZ (US)

(72) Inventor: Brenda McCaffrey, Phoenix, AZ (US)

( * ) Notice: Subject to any disclaimer, the term of this patent is extended or adjusted under 35 U.S.C. 154(b) by 3 days.

(21) Appl. No.: 14/172,233

(22) Filed: Feb. 4, 2014

(65) Prior Publication Data

US 2014/0221855 A1 Aug. 7, 2014

Related U.S. Application Data

(60) Provisional application No. 61/761,341, filed on Feb. 6, 2013.

(51) Int. Cl.
*A61B 5/0452* (2006.01)
*A61B 5/00* (2006.01)
*A61B 5/024* (2006.01)

(52) U.S. Cl.
CPC .................. *A61B 5/486* (2013.01); *A61B 5/024* (2013.01); *A61B 5/742* (2013.01); *A61B 5/681* (2013.01); *A61B 5/6823* (2013.01)

(58) Field of Classification Search
CPC ..................................................... A61B 5/0452
USPC .......................................... 600/300, 407, 508
See application file for complete search history.

(56) References Cited

U.S. PATENT DOCUMENTS

2013/0096843 A1* 4/2013 Yuen et al. ...................... 702/19

* cited by examiner

*Primary Examiner* — Nicole F Lavert
*Assistant Examiner* — Nadia A Mahmood
(74) *Attorney, Agent, or Firm* — Robert D. Atkins; Patent Law Group: Atkins and Associates, P.C.

(57) ABSTRACT

A biofeedback device is configured to be worn by a user. The biofeedback device includes one or more sensors and may include a transmitter. A physiological parameter of the user is measured with the sensor to obtain a measurement. The measurement is transmitted to a receiver. A receiver is configured to receive the measurement from the sensor. A plurality of ranges for the physiological parameter are defined based on a characteristic of the user. The biofeedback device includes a processor coupled to the sensor. The processor compares the measurement to the plurality of ranges. A display is coupled to the processor. The display is activated based on the measurement and the data ranges. The display provides a first output according to a first range of the plurality of ranges corresponding to the measurement. A first color is displayed based on a first range corresponding to the measurement.

25 Claims, 10 Drawing Sheets

DEVICE AND METHOD FOR DISPLAYING BIOFEEDBACK

CLAIM TO DOMESTIC PRIORITY

The present application claims the benefit of U.S. Provisional Application No. 61/761,341, filed Feb. 6, 2013, which application is incorporated herein by reference.

FIELD OF THE INVENTION

The present invention relates to physiological monitoring and display systems, more particularly, to a system and method of receiving information from a sensor and displaying the information in a wearable device.

BACKGROUND OF THE INVENTION

Physiological information is useful for self-monitoring of one's personal health and fitness. Monitoring a person's physiological characteristics can be used to provide biofeedback about one's physiological state. A biofeedback device makes information about bodily processes perceptible to the senses, allowing the person to interpret the biofeedback information and react or alter one's activity in order to help control one's involuntary bodily processes. Various physiological characteristics can be monitored during physical activity or other activities. For example, a heart rate monitor is worn on the body to continuously or periodically measure heart rate. The heart rate can be transmitted to a device, such as a computer, which processes the signal and displays the heart rate information in the form of text, numbers, or a graph.

Wearable devices for receiving and displaying physiological information are often complicated devices displaying alphanumeric text to communicate a multitude of data points and statistics. Complex display devices, such as performance watches, display various types of personal data, such as heart rate as beats per minute or as a percentage of maximum heart rate, calories burned, time lapsed, lap time, lap count, distance, speed, acceleration, pace, pedal rotations or cycling cadence, elevation, altitude, incline, temperature, and other information about a person's activity or environment. Information is typically displayed in the form of alphanumeric text or in a graphical manner. Digital text, numbers, and charts displayed on a relatively small display screen, such as on a watch face, can be difficult to read and interpret during physical activity. Complex wearable devices are bulky and can contain an overwhelming amount of data that can actually interfere with the user's performance during an activity, rather than enhance performance. The device may take a user's attention away from an activity for several seconds while the user views the data. The distraction caused by a complex display of information can be merely interruptive, but can also be dangerous, for example, when a user takes his or her eyes off of the road.

Fitness and sport watches, for example, often include blinking lights or notification sounds or vibration to alert the user to a particular parameter or end point. However, intrusive lights and sounds are disruptive to certain types of activities and exercise. Other wearable devices record physiological data, but require a computer in order to upload and display the data after an activity. A user receives performance data after the activity and after the time has passed when the user can react and use the performance data. While past physiological data is useful for some purposes, real-time monitoring is more useful to allow the user to adjust his or her performance during an activity.

SUMMARY OF THE INVENTION

A need exists to monitor and display physiological or biometric information in a manner that is easy for a user to interpret and understand. Accordingly, in one embodiment, the present invention is a method of providing biofeedback comprising the steps of providing a sensor, measuring with the sensor a physiological parameter of a user to obtain a measurement, receiving the measurement from the sensor, defining a plurality of ranges for the physiological parameter, comparing the measurement to the plurality of ranges, and displaying a first color based on a first range of the plurality of ranges corresponding to the measurement.

In another embodiment, the present invention is a method of providing biofeedback comprising the steps of providing a biofeedback device including a display, inputting a plurality of data ranges into the biofeedback device, sensing a physiological parameter of a user, comparing the physiological parameter to the data ranges, and activating the display of the biofeedback device based on the physiological parameter and the data ranges.

In another embodiment, the present invention is a biofeedback display device comprising a sensor coupled to a user to collect physiological data. A receiver is configured to receive physiological data from the sensor. A processor is coupled to the receiver. The processor including a plurality of ranges defined for the physiological data. A display is coupled to the processor. The display illuminates with a color according to a first range of the plurality of ranges corresponding to the physiological data.

In another embodiment, the present invention is a biofeedback display device comprising a sensor coupled to a user to obtain a measurement. A processor is coupled to the sensor. The processor includes a plurality of ranges defined for the measurement. A display is coupled to the processor. The display provides a first output according to a first range of the plurality of ranges corresponding to the measurement.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Figure 1:
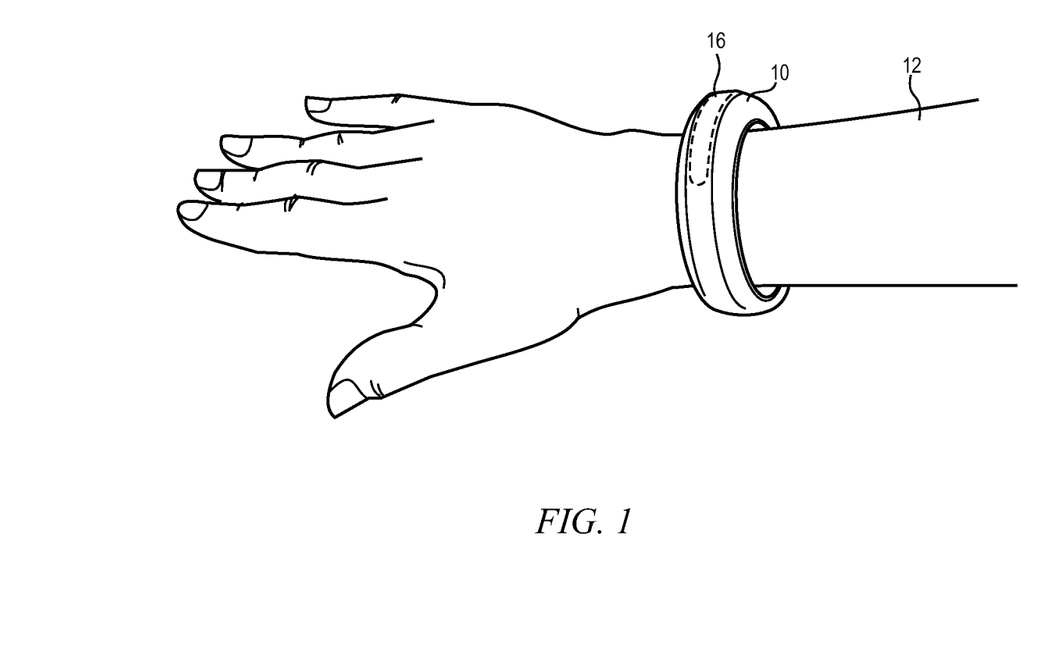
FIG. 1 illustrates a method of using a biofeedback display device.

FIG. 1 shows a method of using a biofeedback display device. In FIG. 1, biofeedback device 10 is worn on the wrist of user 12. Biofeedback device 10 is a display device that is configured to display physiological information, or biofeedback, to user 12. Biofeedback device 10 is worn by user 12 as part of a biofeedback system that collects physiological data about user 12, interprets the data, and displays the interpreted data for user 12. Biofeedback device 10 is used to bring awareness to the user's physiological condition.

Biofeedback device 10 is a portable device that is wearable as an accessory or built into an article of clothing. In one embodiment, biofeedback device 10 includes a bracelet or wrist band, which is worn on the wrist or arm. In another embodiment, biofeedback device 10 includes a shirt, jacket, glove, shoe, bag, or other article of clothing or accessory. In yet another embodiment, biofeedback device 10 includes a portable unit that can be easily attached to user 12 or carried by user 12.

Biofeedback device 10 includes a display area 16 where biofeedback information is displayed to user 12. Display area 16 is configured to display a light, color, image, or graphic to user 12. Display area 16 may include a light, an array of lights, a liquid crystal display (LCD) screen, a light emitting diode (LED) screen, a touchscreen, or other suitable display. Display area 16 includes a portion of a surface of biofeedback device 10. In one embodiment, the non-display portion of biofeedback device 10 is opaque. Alternatively, display area 16 includes the entire outer surface of biofeedback device 10. For example, display area 16 includes a translucent or transparent material. A colored light, such as an LED or LED array, is disposed within biofeedback device 10. When the light is activated, the light or color illuminates biofeedback device 10 and the light or color is visible by user 12 through the translucent material. Light passes through display area 16, which includes a portion of the outer surface of biofeedback device 10.

In one embodiment, display area 16 illuminates with a plurality of colors to communicate biofeedback information to user 12. Display area 16 is configured to display the color as a soft, diffusely lighted color. Biofeedback device 10 displays information using subtle light and color in order to provide biofeedback to user 12 in an unobtrusive manner so the user 12 can choose to respond to or ignore the display. The lighted color display format of biofeedback device 10 is viewable in the user's the peripheral vision. Display area 16 is easily viewed by user 12 even when user 12 is not looking directly at the biofeedback device 10. User 12 is able to see the color illuminated in display area 16 without taking focus or concentration away from the user's activity or task. Therefore, user 12 passively receives continuous biofeedback from biofeedback device 10. The continuous biofeedback from biofeedback device 10 can be used by user 12 to monitor the user's own health or performance in real time.

Figure 2:
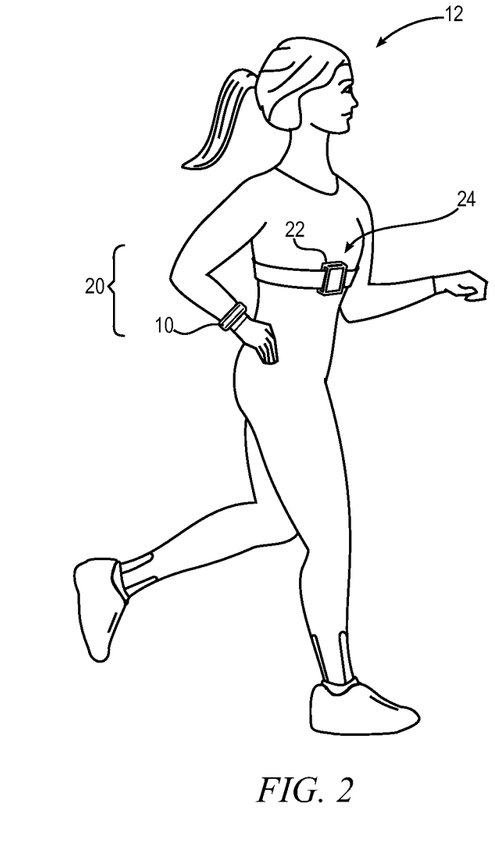
FIG. 2 illustrates a method of using a biofeedback display device.

FIG. 2 shows a method of using biofeedback device 10 with a sensor, such as a heart rate monitor. Biofeedback system 20 includes a sensor 22 wirelessly coupled to biofeedback device 10. One or more sensors 22 are coupled to user 12 to detect and measure physiological information about user 12 or environmental information about the user's surroundings. Sensor 22 is any type of sensor that suits the needs of user 12. Sensor 22 is coupled directly to user 12, worn on the clothing or skin of user 12, carried by user 12, or placed in proximity to user 12 depending on the type of sensor 22.

Sensor 22 detects physiological, performance, environmental, or other type of information to be displayed by biofeedback device 10. Physiological information that can be sensed or detected by sensor 22 and used for biofeedback includes heart rate, breathing rate, skin temperature, skin resistivity, electrocardiogram (ECG), electroencephalogram (EEG), electromyogram (EMG), blood pressure, body temperature, muscle tension, blood glucose levels, oxygen saturation, calorie expenditure, and other physiological parameters. Performance data can also be measured using sensor 22 and provided as biofeedback. Performance data includes speed, acceleration, distance, time lapsed, pace, pedal rotations or cycling cadence, altitude, lap count, lap time, calories burned, and other performance parameters. Information about the user's environment can also be detected using sensor 22 and displayed using biofeedback device 10. Environmental information includes global positioning system (GPS) location, ambient temperature, humidity, altitude, atmospheric pressure, airborne particulates or pollutants, air quality, chemical exposure, radiation, electromagnetic field, or other environmental parameters. Sensor 22 is selected according to the biofeedback or information desired by user 12.

Biofeedback device 10 wirelessly receives physiological information from one or more sensors 22 disposed on or in proximity to user 12. Biofeedback device 10 processes the physiological information from sensor 22 and produces a display correlating to the processed physiological information. Biofeedback device 10 thereby provides biofeedback by sensing and reporting physiological information from sensor 22 to user 12 in real time. Biofeedback can be used during exercise, training, rehabilitation, behavior therapy, medical diagnostics, at work, or in a home setting. The biofeedback information provided to user 12 by biofeedback device 10 enables user 12 to self-regulate the user's activity and behavior in order to improve the user's performance or health.

In one embodiment, biofeedback device 10 is configured to receive data transmitted from a heart rate monitor 24, which includes sensor 22 for detecting an ECG signal or heart rate data. Heart rate can be measured using noninvasive methods. Noninvasive heart rate monitoring typically uses one of two types of monitors, a chest strap sensor or a finger sensor. A chest strap heart rate monitor includes electrodes that are placed in contact with the user's skin and worn in proximity to the user's heart. The electrical signal from the user's heart is detected at the electrode-skin interface and is transmitted by heart rate monitor 22 to biofeedback device 10. A finger sensor heart rate monitor uses plethysmography, infrared light sensors, or capacitance to measure heart rate. A finger sensor is worn on the finger to detect heart rate and transmit the heart rate data to biofeedback device 10.

Figure 3:
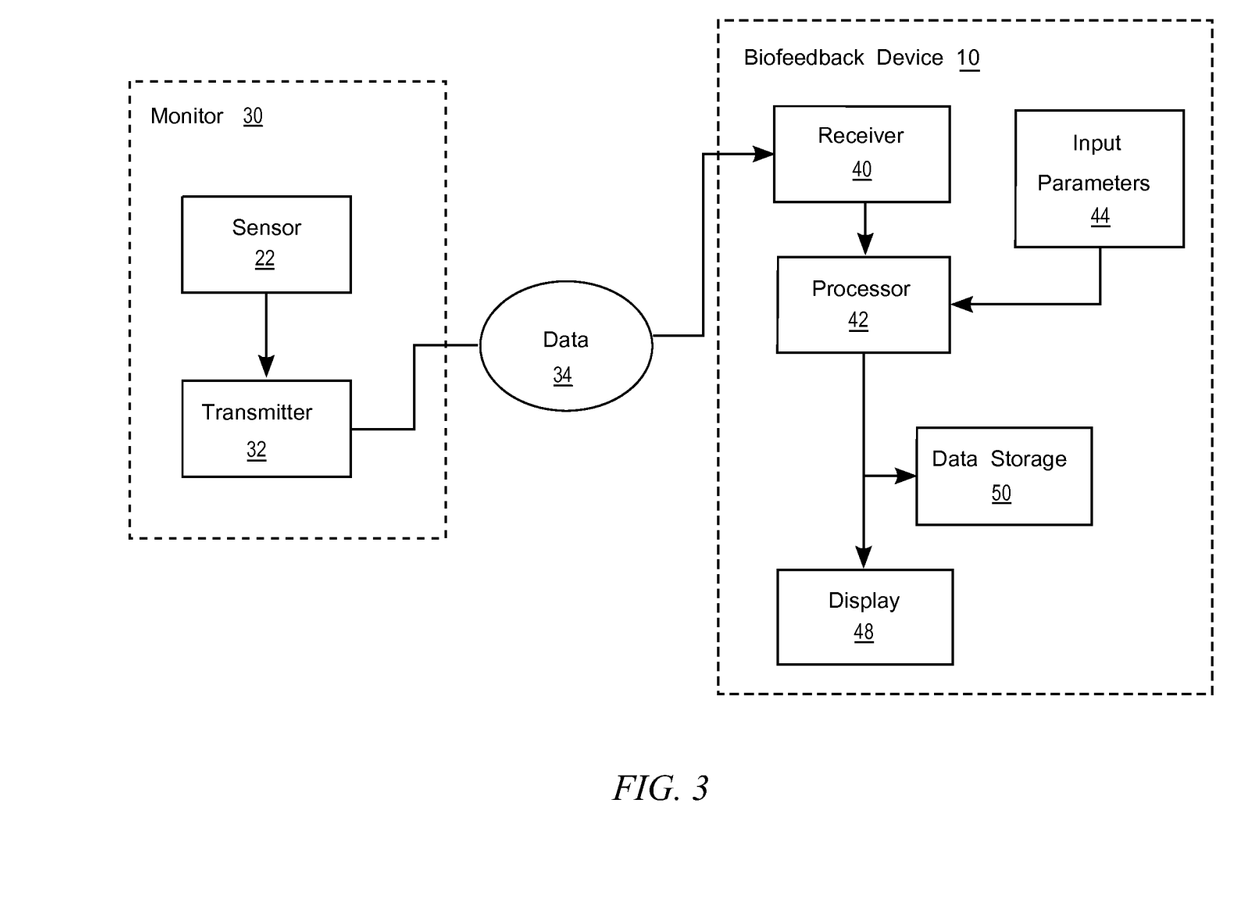
FIG. 3 illustrates a biofeedback system with a biofeedback display device.

FIG. 3 shows a block diagram of biofeedback system 20. Monitor 30 includes sensor 22 and transmitter 32. Sensor 22 measures a physiological, performance, or environmental parameter and generates a measurement or data 34. Data 34 may be an analog or digital signal. In one embodiment, data 34 is a raw heart rate measurement or an averaged heart rate, such as beats per minute. Transmitter 32 transmits data 34 wirelessly to biofeedback device 10. Transmitter 32 transmits data 34 using a wireless protocol, such as Bluetooth Low Energy (BLE), Bluetooth, near field communication (NFC), zigbee, Z-wave, IEEE 802.15.3, ECMA-368, ANT+, or a similar personal area network (PAN) or short-range wireless protocol. Biofeedback device 10 includes a receiver 40, which receives data 34 from transmitter 32. Receiver 40 receives radio frequencies including the 868 MHZ, 915 MHz, 2.4 GHz, and 5.8 GHz bands or ultra wide band (UWB)

frequencies and employs one or more of the BLE, Bluetooth, NFC, zigbee, Z-wave, IEEE 802.15.3, ECMA-368, ANT+, or a similar PAN protocol or short-range wireless protocol.

Biofeedback device 10 further includes a processor 42, which processes and analyzes data 34. Processor 42 includes a microprocessor or other signal processing circuits. Processor 42 is programmed with an algorithm or plurality of algorithms for processing data 34. The algorithm is customized according to the type of sensor 22 and is also customized according to the needs and characteristics of user 12. A plurality of input parameters 44 are encoded within processor 42. Input parameters 44 may include information about user 12, such as age, height, weight, basal metabolic rate, maximum heart rate, or other physical, biological, or physiological parameters. Input parameters 44 may also include a set of ranges, parameters, or end points for data 34, where the ranges are personalized for user 12. The ranges correlate to measurements or data 34 from sensor 22. Input parameters 44 are used by processor 42 to interpret data 34 according to personalized parameters for user 12.

Processor 42 compares data 34 to input parameters 44. Processor 42 optionally filters, conditions, or transforms data 34 prior to comparing data 34 to input parameters 44. In one embodiment, input parameters 44 include a plurality of ranges based on the personal information of user 12. For example, a maximum heart rate for user 12 is determined based on the user's age as entered by user 12 into biofeedback device 10. Ranges are programmed as a percentage of maximum heart rate. For example, a first range is designated as 60% to 70% of the user's maximum heart rate, a second range is designated as 70% to 80% of the user's maximum heart rate, and a third range is designated as 80% to 90% of the user's maximum heart rate.

In another embodiment, input parameters 44 include a plurality of ranges entered by user 12. For example, user 12 enters a maximum heart rate or enters the heart rate ranges preferred by user 12. The pre-programmed or manually-entered ranges each includes a plurality of values for data 34 that correlate to the range. Processor 42 determines which range data 34 falls into. Processor 42 activates or triggers display 48 according to the range into which data 34 falls. Therefore, in one embodiment, processor 42 interprets data 34 by comparing data 34 to input parameters 44 and assigning data 34 to a range.

Biofeedback device 10 includes display 48, which displays the output of processor 42. Display 48 includes a plurality of display outputs which correspond to the ranges inputted as input parameters 44. When data 34 is determined by processor 42 to fall within a first range, processor 42 provides a first output. A first output is displayed by display 48. When data 34 is determined by processor 42 to fall within a second range, processor 42 provides a second output. A second output is displayed by display 48. The second output is easily distinguished by user 12 from the first output. Any number of different ranges or parameters may be specified to produce an output.

In one embodiment, display 48 includes an array or a plurality of LEDs. The LEDs may include multi-color LEDs, such as duel-color or tri-color LEDs, and single-color LEDs. In one embodiment, the LEDs are multi-color LEDs, for example, red-green-blue LEDs or other color configurations of multi-color LEDs. In another embodiment, display 48 includes an array or a plurality of single-color LEDs. Each output from processor 42 is displayed as a different color by display 48. Each output, or color, corresponds to a particular range. Biofeedback device 10 displays a color to indicate where data 34 falls within the predetermined ranges or parameters. For example, when data 34 indicates the user's heart rate is within 60% to 70% of the user's maximum heart rate, processor 42 provides an output to activate the blue LED or blue portion of a multi-color LED in display 48. Similarly, when data 34 indicates the user's heart rate is within 70% to 80% of the user's maximum heart rate, processor 42 provides an output to activate the green LED or green portion of a multi-color LED in display 48. When data 34 indicates the user's heart rate is within 80% to 90% of the user's maximum heart rate, processor 42 provides an output to activate the red LED or red portion of a multi-color LED in display 48. Display 48 is configured with any number of colors or display characteristics that indicate a biofeedback parameter of user 12. The features and colors of display 48 can be selected by user 12 or customized for user 12 according to the user's needs. By displaying biofeedback in the form of a color, by associating each color with a range, the biofeedback displayed to user 12 is simplified and user-friendly.

User 12 notices the color displayed by biofeedback device 10 and understands where the user's physiological state falls within the predetermined parameters. In one embodiment, biofeedback device 10 does not display alphanumeric text that requires a user to look directly at biofeedback device. Rather, biofeedback device 10 illuminates with a color that can be detected by user 12 in the user's peripheral vision. Further, because the color indicates the range in which the user's data 34 falls, the information is already processed by processor 42 and simplified before the biofeedback reaches user 12. User 12 does not need to mentally process the information displayed other than to recognize the color and understand the meaning associated with the color. Display 48 of biofeedback device 10 provides an uncomplicated and non-disruptive biofeedback display.

The color output of display 48 as well as input parameters 44 can be selected and programmed by user 12. User 12 selects each range, parameter, or end point for data 34 and selects each color or display output correlating to each range, parameter, or end point. Where user 12 determines input parameters 44 and display outputs, the output of biofeedback device 10 can be easily interpreted and understood by user 12, but is not readily apparent to others. Therefore, biofeedback device 10 can be customized for each user, and allow user 12 a more personalized and private display of biofeedback information.

Biofeedback device 10 may include memory or data storage 50, which stores data 34 received from transmitter 32 of monitor 30. Memory or data storage 50 may include read-only memory (ROM), programmable read-only memory (PROM), erasable programmable read-only memory (EPROM), electrically erasable programmable read-only memory (EEPROM), serial EPROM, magneto-resistive random-access memory (MRAM), ferro-electric RAM (F-RAM), phase-change RAM (PRAM), flash memory, or other non-volatile memory. By storing data 34, data 34 can be used for real time biofeedback as well as for later evaluation of data 34.

Biofeedback device 10 optionally includes a transmitter for sending data 34 prior to or after processor 42 processes data 34. Biofeedback device 10 may transmit data 34 wirelessly to a computer, such as a desktop computer, laptop computer, tablet computer, smartphone, or other computing device. Biofeedback device 10 may transmit data 34 in real time or after data 34 has been stored by biofeedback device 10.

Figure 4:
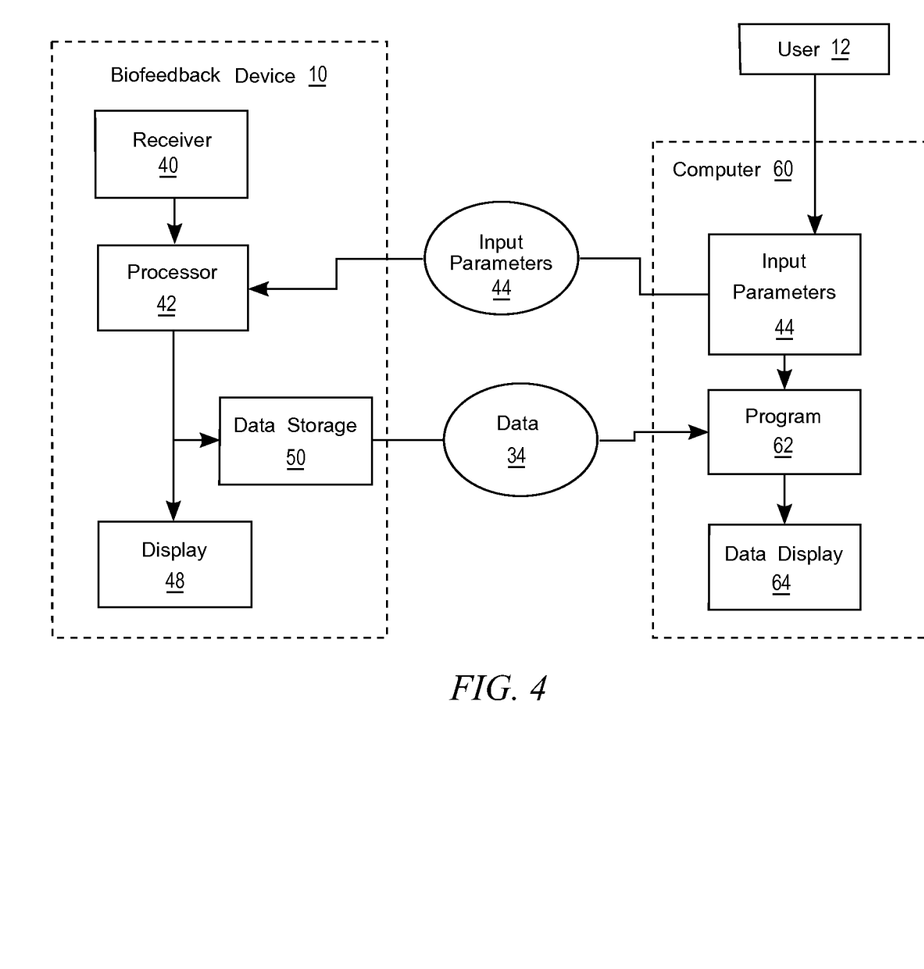
FIG. 4 illustrates another method of using a biofeedback device.

FIG. 4 shows a block diagram of a method of using a biofeedback device. Biofeedback device 10 is configured to couple to computer 60. Computer 60 may be a desktop computer, laptop computer, tablet computer, smartphone, or other computing device. In one embodiment, data 34 received by biofeedback device 10 is stored by data storage 50. Data 34 is stored before or after processor 42 has processed data 34. Data 34 stored by data storage 50 is available to upload to computer 60 after data 34 has been collected. Data 34 is transmitted or transferred from biofeedback device 10 to computer 60 by wireless or hard-wire connection. Biofeedback device 10 optionally includes a transmitter that wirelessly transmits data 34 to computer 60 using BLE, Bluetooth, NFC, zigbee, Z-wave, IEEE 802.15.3, ECMA-368, ANT+, a Wi-Fi protocol such as IEEE 802.11a, IEEE 802.11b, IEEE 802.11g, IEEE 802.11n, Wi-Fi direct, or a similar PAN or short-range wireless protocol.

Computer 60 includes a user interface, application, or program 62. Using computer 60, user 12 enters input parameters 44 into program 62. In one embodiment, biofeedback device 10 includes a port, such as a universal serial bus (USB) port, mini USB, micro USB, or other data port, to interface with computer 60. Input parameters 44 are entered by user 12 into program 62 which are used by processor 42. Alternatively, input parameters 44 are preprogrammed into processor 42 and a user interface with processor 42 is not required. Input parameters 44 can be used to select the display mode according to the user's needs. For example, user 12 can program processor 42 with a particular range or parameter and correlate the parameter to a display output, such as a color. Accordingly, biofeedback device 10 is customized and personalized for user 12.

Figure 5:
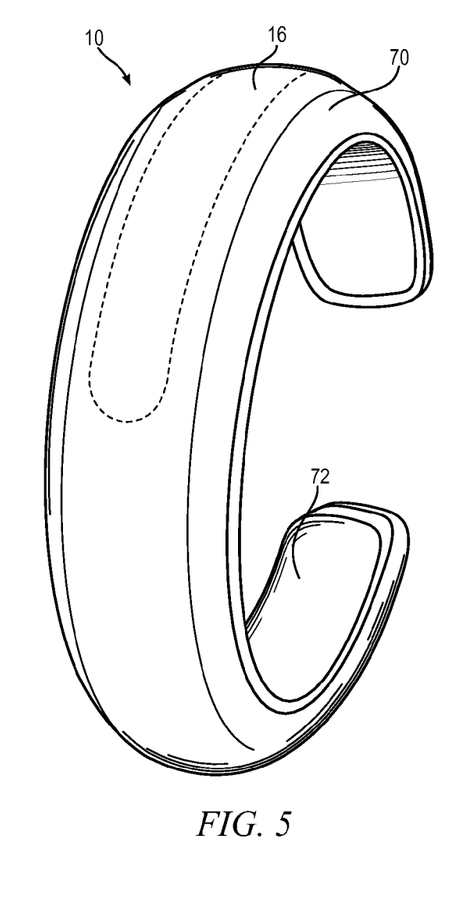
FIG. 5 illustrates a biofeedback device.

FIG. 5 shows biofeedback device 10 incorporated into an accessory. Biofeedback device 10 is portable and can be built into clothing or accessories. In one embodiment, biofeedback device 10 is a wearable accessory. In another embodiment, biofeedback device 10 is attached to user 12. In an alternative embodiment, biofeedback device 10 is incorporated into a fabric which can be worn as clothing. As part of an accessory, such as a bracelet or wrist band, biofeedback device 10 can be rigid or flexible. In one embodiment, biofeedback device 10 includes a shell 70 comprised of a rigid polymer with the electronic components disposed within shell 70. Shell 70 may include a plastic or polymer, such as acrylonitrile butadiene styrene (ABS), polylactic acid (PLA), polyamide, nylon, acrylic, polyethylene terephthalate (PET), acetate film, polypropylene, polyurethane, polyethylene (PE), ultra high molecular weight PE (UHMW), polyamide, polytetrafluoroethylene (PTFE), polyvinyl fluoride (PVF), polyvinyl alcohol (PVA), polyvinyl chloride (PVC), polystyrene, or other suitable material. Shell 70 may include glass, coated glass, chemically strengthened glass, rubber, metal, natural materials, or a combination of materials.

Shell 70 further includes inner shell 72. Inner shell 72 comprises the same material as shell 70 or comprises a different material. Shell 70 and inner shell 72 fit together to enclose the internal components of biofeedback device 10. Shell 70 of biofeedback device 10 includes display area 16. In one embodiment, display area 16 is a translucent or transparent portion of shell 70. A material is selected for shell 70 to allow an internal light to transmit through the material such that the light is viewable on the outer surface of shell 70. A translucent material of shell 70 allows display area 16 to illuminate with a soft, diffuse light or lighted color. A material is selected for shell 70 to reflect and amplify the light in display 48, thereby reducing the power required to illuminate display area 16. In one embodiment, a multi-color LED, tri-color LED, or LED array is disposed internal to biofeedback device 10 within shell 70 and inner shell 72. When one or more LEDs are activated, the color is visible through display area 16. In one embodiment, display area 16 is a portion of shell 70 having a reduced thickness to increase the transmittance of light through shell 70. In another embodiment, additional portions of shell 70 outside of display area 16 are illuminated when display area 16 is also illuminated. The display area 16 is not confined to one area of biofeedback device. The entire shell 70 may illuminate with the color of the LED. In another embodiment, shell 70 is transparent and the internal components of biofeedback device are visible. In yet another embodiment, shell 70 includes an opening and the display is visible through the opening. Display area 16 is a light, light array, LCD screen, LED screen, touchscreen, or other suitable display.

Display area 16 is configured to display a plurality of colors with each color correlating to a biofeedback parameter. As biofeedback device 10 receives information from transmitter 32, biofeedback device 10 communicates the information to user 12 by illuminating display area 16 with a color. User 12 recognizes the color and the meaning of the color and can decide whether to modify a behavior or activity in response to the biofeedback.

Display area 16 additionally may display a notification. A notification may indicate user 12 has received a call, a text, or other personalized message. Biofeedback device 10 is wirelessly coupled to computer 60, which may be a smartphone. When a call or text message is received by computer 60, biofeedback device 10 receives a notification wirelessly through receiver 40. Biofeedback device 10 displays the notification as a light, color, or image in display area 16.

Figure 6:
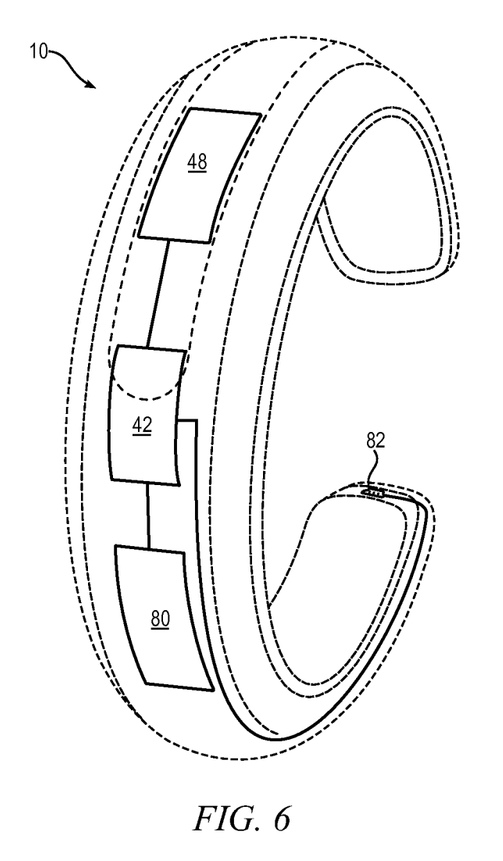
FIG. 6 illustrates another view of a biofeedback device.

FIG. 6 shows an alternative view biofeedback device 10 including a block diagram of the internal components of biofeedback device 10. Biofeedback device 10 includes processor 42 disposed internally within shell 70. Biofeedback device 10 includes a receiver for receiving a signal from a transmitter. Processor 42, receiver 40, and display 48 are powered by power source or battery 80. In one embodiment, battery 80 is a flexible rechargeable lithium polymer battery. Data port 82 is coupled to processor 42. Data port 82 is used for hard-wire transfer of data 34 to computer 60. Data port 82 may include a USB port, mini USB, micro USB, or other connection. Data port 82 is coupled to battery 80. Biofeedback device 10 couples to an external power source through data port 82. Data port 82 provides a connection to a power source for charging battery 80. Alternatively, battery 80 is charged by inductive charging or with an alternative power source. Display 48 is coupled to processor 42 and battery 80. Display 48 includes a plurality of LEDs such as multi-color or tri-color LEDs. Alternatively, the device contains a plurality or an array of single-color LEDs. In one embodiment, display 48 contains a tri-color red-green-blue (RGB) LED.

Figure 7:
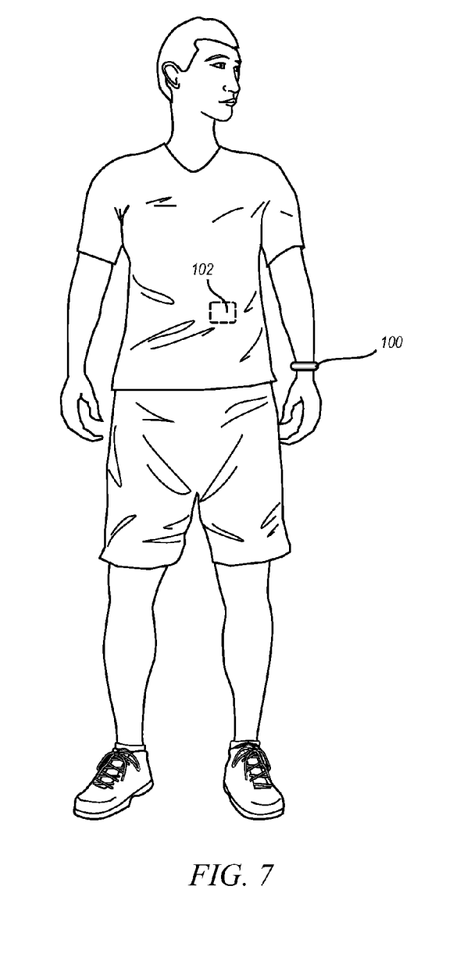
FIG. 7 illustrates an alternative method of using a biofeedback device.

FIG. 7 shows an alternative method of using biofeedback device 10. Biofeedback device 100 is similar to biofeedback device 10 and is configured to receive data transmitted from one or more sensors. The biofeedback system includes monitor 102, which comprises a sensor and a transmitter. Monitor 102 is coupled to user 12. Monitor 102 includes a sensor for detecting breathing rate, skin temperature, skin resistivity, ECG, EEG, EMG, blood pressure, temperature, muscle tension, blood glucose levels, oxygen saturation, or other physiological condition. Biofeedback device 100 can be configured to receive data from multiple sensors disposed on user 12 or in proximity to user 12.

In one embodiment, biofeedback device 100 is configured to receive blood glucose data from a continuous blood glucose monitor. A continuous glucose monitor uses an electrode placed under the surface of the skin to measure glucose levels within a user's tissue. The continuous glucose monitor transmits blood glucose data to a receiver in biofeedback device 100. Biofeedback device 100 displays blood glucose according to assigned ranges inputted into biofeedback device 100.

In another embodiment, biofeedback device 100 is configured to receive breathing rate data from a spirometer or other air flow or lung volume monitoring device. For example, a pressure transducer is disposed on the chest of user 12 and used to monitor the volume of the lungs, tidal volume, total lung capacity, expiratory reserve volume, or residual volume. The monitor transmits breathing data to biofeedback device 100. Biofeedback device 100 displays breathing rate according to assigned ranges inputted into biofeedback device 100.

In another embodiment, biofeedback device 100 is configured to receive skin temperature and skin resistivity data. Skin temperature is measured noninvasively using a thermistor, thermocouple, thermometer, or other temperatures measurement device. Skin resistivity is measured using one or more electrodes disposed on the skin surface to measure the moisture at the skin's surface. Biofeedback device 100 received skin temperature and skin resistivity data from a sensor. Biofeedback device 100 processes the data and displays biofeedback to user 12.

In another embodiment, biofeedback device 100 is configured to receive EEG data or EMG data from one or more skin sensors. EEG signals, or brainwaves, are measured noninvasively in an ambulatory setting using electrodes disposed on the user's head. Similarly EMG measures muscle activity or muscle tension. Biofeedback device 100 provides user 12 with information about brain and muscle activity.

In another embodiment, biofeedback device 10 is configured to receive blood pressure data from a blood pressure sensor. Blood pressure can be measured noninvasively using an oscillometric method, which uses a cuff and a pressure transducer to determine the user's blood pressure. Biofeedback device 100 displays blood pressure according to assigned ranges inputted into biofeedback device 100.

In another embodiment, biofeedback device 100 is configured to receive oxygen saturation data from a plethysmographic sensor, or pulse oximetry sensor. Blood oxygen saturation is measured noninvasively using a sensor placed on the finger of user 12. Biofeedback device 100 displays oxygen saturation according to assigned ranges inputted into biofeedback device 100.

Accordingly, biofeedback device 100 provides personal biofeedback customized for user 12. Biofeedback allows user 12 to learn about the user's personal physiological state and physiological responses. By continuously monitoring one or more physiological parameters, user 12 can respond to the data and modify behavior or activity to improve health and performance.

Figure 8:
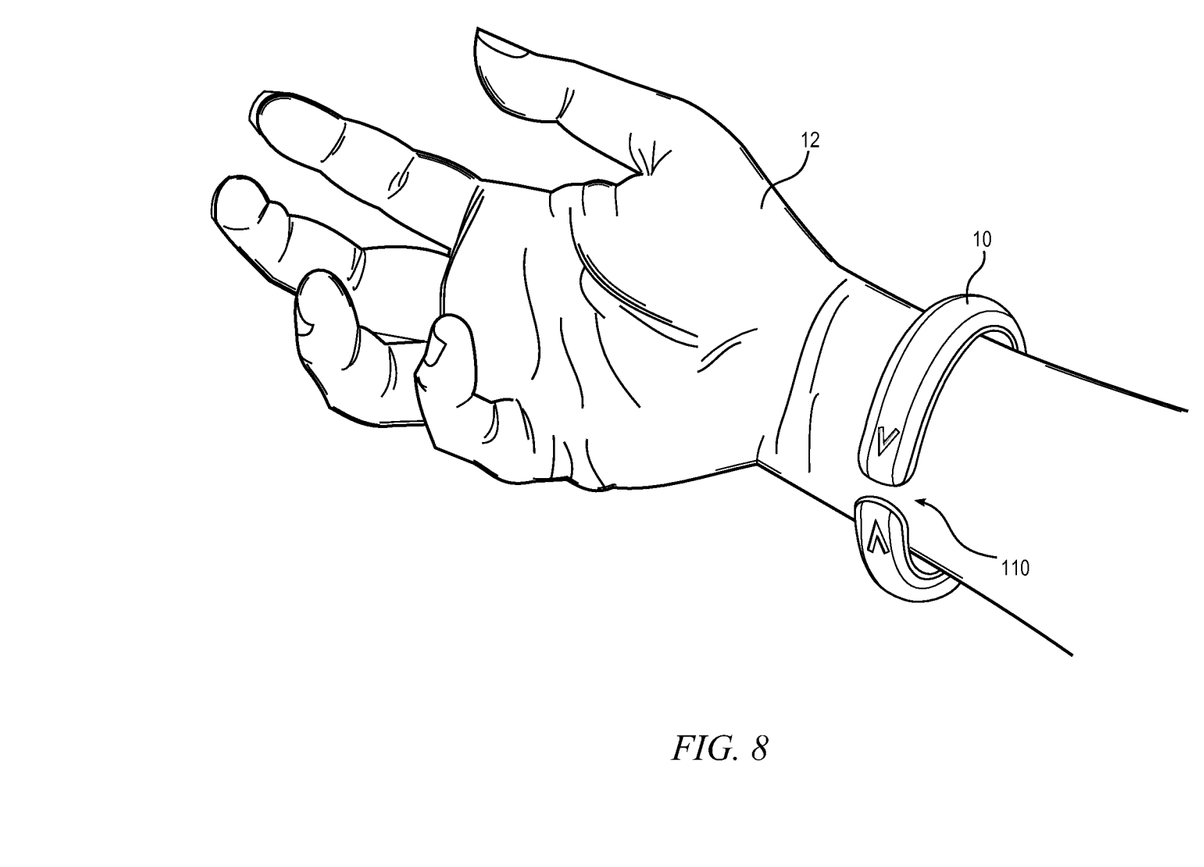
FIG. 8 illustrates another view of a biofeedback device.

FIG. 8 shows another view of biofeedback device 10 worn on the wrist of user 12. Biofeedback device 10 is incorporated into a bracelet or wristband. Biofeedback device 10 is designed to be worn by user 12 during most activities, including exercise, relaxation, sleep, and work. Biofeedback device 10 resembles a piece of jewelry in order to disguise the device, such that the biofeedback is more private to user 12. The shape of biofeedback device 10 provides a loose or tight fit around the user's wrist. An opening 110 in the generally circular shape allows user 12 to slip the device on and off the wrist. The opening 110 is placed on a side of the user's wrist to reduce movement of the loose-fitting band. User 12 slides biofeedback device 10 up higher on the arm for a tighter fit. Therefore, biofeedback device 10 provides a loose comfortable fit or a tight fit according to the needs and different activities of user 12. Opening 110 helps maintain a position of biofeedback device 10 on the arm of user 12.

Figure 9:
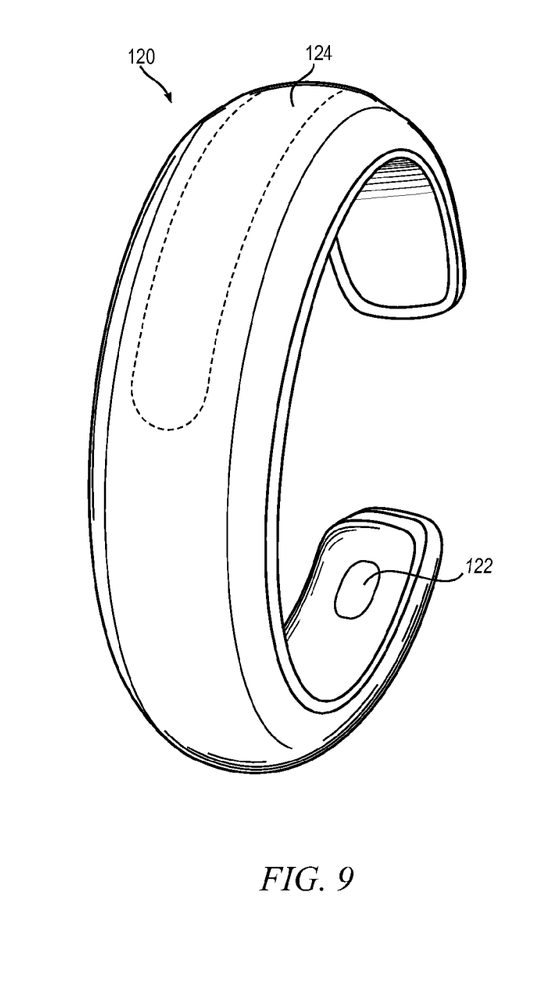
FIG. 9 illustrates an alternative biofeedback device with a built-in sensor.

FIG. 9 shows an alternative embodiment of an alternative biofeedback device. Biofeedback device 120 includes a sensor 122 and display incorporated into a single biofeedback device 120. Sensor 122 is built into biofeedback device 120 and provides a complete biofeedback system in one unit. A separate monitor with a sensor and transmitter is not required for biofeedback device 120. Biofeedback device 120 includes display area 124. Display area 124 is similar to display area 16 of biofeedback device 10. Display area 124 is configured to display a light, color, image, or graphic to user 12. Display area 124 may include a light, an array of lights, an LCD screen, an LED screen, a touchscreen, or other suitable display. Display area 124 includes a portion of a surface of biofeedback device 10. Alternatively, display area 124 includes the entire outer surface of biofeedback device 120.

In one embodiment, display area 124 illuminates with a plurality of colors to communicate biofeedback information to user 12. Display area 124 is configured to display the color as a soft, diffusely lighted color. Biofeedback device 120 displays information using subtle light and color in order to provide biofeedback to user 12 in an unobtrusive manner so the user 12 can choose to respond to the display or to ignore the display. The lighted color display format of biofeedback device 120 is viewable in the user's peripheral vision. Display area 124 is easily viewed by user 12 even when user 12 is not looking directly at the biofeedback device 120. User 12 is able to see the color illuminated in display area 124 without taking focus or concentration away from the user's activity or task. Therefore, user 12 passively receives continuous biofeedback from biofeedback device 120. The continuous biofeedback from biofeedback device 120 can be used by user 12 to monitor the user's own health or performance in real time.

Figure 10:
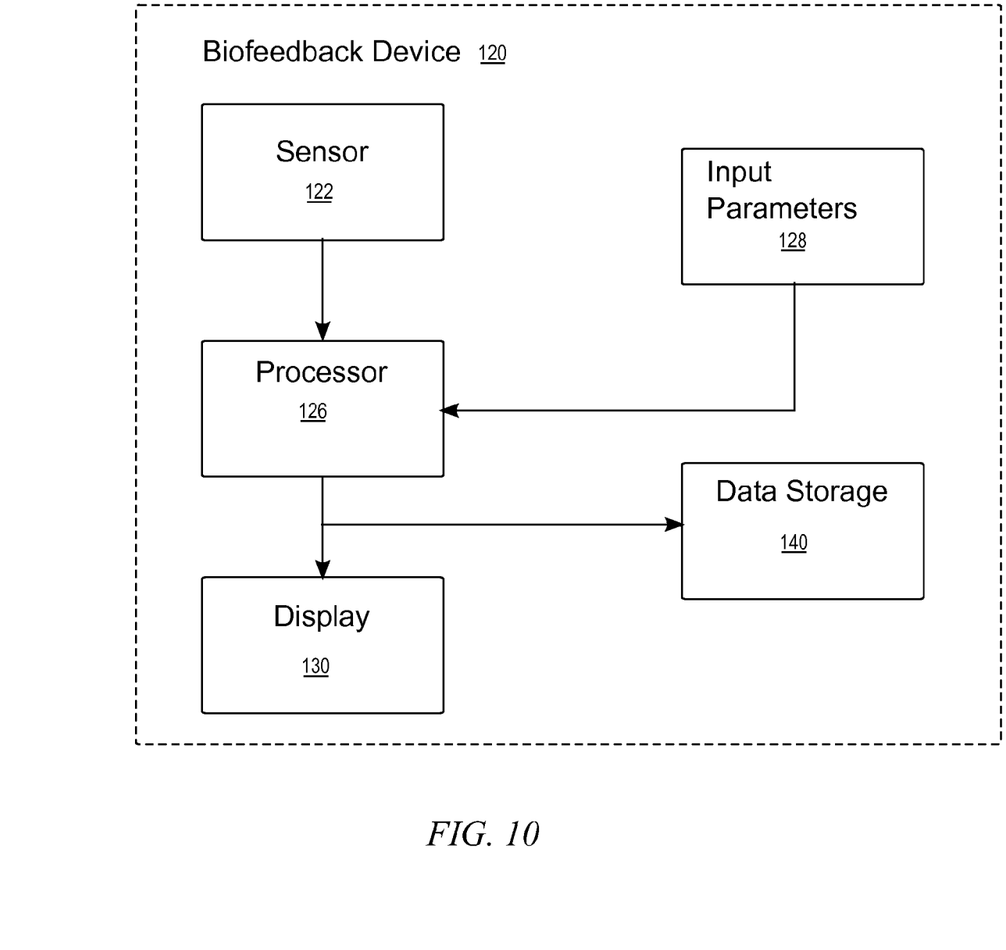
FIG. 10 illustrates a method of using an alternative biofeedback device.

FIG. 10 shows a block diagram of an alternative biofeedback device. Biofeedback device 120 is a biofeedback system. Biofeedback device 120 includes sensor 122 and processor 126. Processor 126 is similar to processor 42. Processor 126 includes a microprocessor or other signal processing circuits. Processor 126 is programmed with an algorithm or plurality of algorithms for processing biofeedback information or data. The algorithm is customized according to the type of sensor 122 and is also customized according to the needs and characteristics of user 12. A plurality of input parameters 128 are encoded within processor 126. Input parameters 128 may include information about user 12, such as age, height, weight, basal metabolic rate, maximum heart rate, or other physical, biological, or physiological parameters. Input parameters 128 may also include a set of ranges, parameters, or end points for the data collected by sensor 122, where the ranges are personalized for user 12. The ranges correlate to measurements or data from sensor 122. Input parameters 128 are used by processor 126 to interpret the data according to personalized parameters for user 12.

Biofeedback device 120 includes display 130, which displays the output of processor 126. Display 130 includes a plurality of display outputs which correspond to the ranges inputted as input parameters 128. Processor 126 activates or triggers display 130 according to the range into which the data falls. Therefore, in one embodiment, processor 126 interprets the data by comparing the data to input parameters 128 and assigning the data to a range. Biofeedback device 120 may include memory or data storage 140, which stores data from sensor 122. By storing the data, the data can be used for real time biofeedback as well as for later evaluation of the data.

While one or more embodiments of the present invention have been illustrated in detail, the skilled artisan will appreciate that modifications and adaptations to those embodiments may be made without departing from the scope of the present invention as set forth in the following claims.

What is claimed is:
1. A method of providing biofeedback, comprising:
  providing a heart rate sensor;
  measuring with the heart rate sensor a heart rate of a user to obtain a heart rate measurement;

receiving the heart rate measurement from the heart rate sensor;

defining a plurality of ranges for the heart rate;

correlating a plurality of colors with the plurality of ranges, a first color of the plurality of colors correlating to a first range of the plurality of ranges and a second color of the plurality of colors correlating to a second range of the plurality of ranges;

comparing the heart rate measurement to the plurality of ranges;

providing a display device configured to be worn by the user;

displaying on the display device the first color when the heart rate measurement is within the first range by continuously illuminating an entire outer surface of the display device with the first color; and displaying on the display device the second color when the heart rate measurement is within the second range by continuously illuminating an entire outer surface of the display device with the second color.

2. The method of claim 1, further including continuously measuring the heart rate of the user.

3. The method of claim 1, further including defining the plurality of ranges according to a characteristic of the user.

4. The method of claim 3, further including displaying the first color and the second color using a plurality of light emitting diodes.

5. The method of claim 1, further including transmitting the heart rate measurement to a computer.

6. The method of claim 1, further including displaying the first color using a plurality of light emitting diodes.

7. A method of providing biofeedback, comprising:
providing a wearable biofeedback device including a display;
inputting a plurality of data ranges into the wearable biofeedback device;
correlating a plurality of colors with the plurality of data ranges;
sensing a physiological parameter of a user;
comparing the physiological parameter to the plurality of data ranges to determine a data range from the plurality of data ranges that includes the physiological parameter; and
illuminating the display of the wearable biofeedback device with a color from the plurality of colors which correlates to the data range that includes the physiological parameter.

8. The method of claim 7, further including sensing the physiological parameter using a heart rate monitor.

9. The method of claim 7, further including:
providing a sensor; and
sensing the physiological parameter using the sensor.

10. The method of claim 7,
wherein illuminating the display further includes continuously illuminating an entire surface of the wearable biofeedback device with the color when the data range includes the physiological parameter.

11. The method of claim 7, further including inputting the plurality of data ranges based on a characteristic of the user.

12. The method of claim 7, further including:
providing a processor; and
filtering the physiological parameter using the processor.

13. The method of claim 7, wherein the wearable biofeedback device is worn on a wrist of the user.

14. A method of providing biofeedback, comprising:
providing a heart rate sensor;
measuring with the heart rate sensor a heart rate of a user to obtain a heart rate measurement;
defining a plurality of ranges for the heart rate of the user;
correlating the plurality of ranges with a plurality of colors;
determining a first range from the plurality of ranges which includes the heart rate measurement;
selecting a first color from the plurality of colors which correlates to the first range;
providing a wearable display device configured to illuminate with the plurality of colors; and
displaying biofeedback to the user by continuously illuminating the first color while the heart rate measurement remains within the first range.

15. The method of claim 14, wherein continuously displaying the first color further includes illuminating an entire display surface of the wearable display device with the first color.

16. The method of claim 14, wherein continuously displaying the first color further includes illuminating an entire outer surface of the wearable display device with the first color.

17. The method of claim 14, wherein the wearable display device is configured to display biofeedback to the user only by illuminating with a color from the plurality of colors.

18. The method of claim 14, further including continuously measuring the heart rate of the user to obtain the heart rate measurement.

19. The method of claim 18, further including continuously displaying a second color from the plurality of colors which correlates to a second range from the plurality of ranges while the heart rate measurement is within the second range.

20. A method of providing biofeedback, comprising:
providing a sensor;
measuring with the sensor a physiological parameter of a user to obtain a measurement;
defining a plurality of ranges for the physiological parameter;
correlating the plurality of ranges with a plurality of colors;
determining a first range from the plurality of ranges which includes the measurement;
selecting a first color from the plurality of colors which correlates to the first range;
providing a display device configured to be worn by the user and to display the plurality of colors; and
continuously displaying the first color while the measurement remains within the first range.

21. The method of claim 20, wherein continuously displaying the first color further includes illuminating an entire display surface of the display device with the first color.

22. The method of claim 20, wherein continuously displaying the first color further includes illuminating an entire outer surface of the display device with the first color.

23. The method of claim 20, wherein the display device is configured to display the measurement to the user only by displaying a color from the plurality of colors.

24. The method of claim 20, further including continuously measuring the physiological parameter of the user to obtain the measurement.

25. The method of claim 20, further including continuously displaying a second color from the plurality of colors which correlates to a second range from the plurality of ranges while the measurement is within the second range.

* * * * *